United States Patent
Benner et al.

(10) Patent No.: US 12,083,217 B1
(45) Date of Patent: Sep. 10, 2024

(54) METHOD OF FABRICATING AN EXTENDED RELEASE SUBCUTANEOUS MEDICINAL DOSAGE IMPLANT SYSTEM

(71) Applicant: DRUG DELIVERY CO., LLC., Salisbury, MD (US)

(72) Inventors: Jeffrey D. Benner, Salisbury, MD (US); Steven M. Cohen, Saint Petersburg, FL (US); Naresh Kumar Reddy Vutukuru, Ann Arbor, MI (US); Pushkar Shrinivas Kulkarni, Ypsilanti, MI (US); Srinivasan Shanmugam, Ypsilanti, MI (US)

(73) Assignee: DRUG DELIVERY CO., LLC., Salisbury, MD (US)

( * ) Notice: Subject to any disclaimer, the term of this patent is extended or adjusted under 35 U.S.C. 154(b) by 477 days.

(21) Appl. No.: 17/456,011

(22) Filed: Nov. 22, 2021

Related U.S. Application Data

(62) Division of application No. 17/301,654, filed on Apr. 9, 2021, now Pat. No. 11,197,819.

(51) Int. Cl.
*A61K 9/00* (2006.01)
*A61K 31/485* (2006.01)
(Continued)

(52) U.S. Cl.
CPC .......... *A61K 9/0024* (2013.01); *A61K 31/485* (2013.01); *A61K 47/02* (2013.01);
(Continued)

(58) Field of Classification Search
CPC ... A61K 9/0024; B29C 45/47; B29K 2071/02
See application file for complete search history.

(56) References Cited

U.S. PATENT DOCUMENTS

| | | |
|---|---|---|
| 6,248,363 B1 | 6/2001 | Patel et al. |
| 6,290,991 B1 | 9/2001 | Roser et al. |

(Continued)

FOREIGN PATENT DOCUMENTS

WO   2006039336 A2 *  4/2006

*Primary Examiner* — Carlos A Azpuru
(74) *Attorney, Agent, or Firm* — Rosenberg, Klein & Lee

(57) ABSTRACT

A method of fabricating an extended release subcutaneous medicinal dosage implant system which includes an implant fabricated from a highly homogeneously mixed composition including a medicinal agent in combination with release controlling polymers which include poly (DL-lactide) and polycaprolactone. In one implementation for treating an opioid disease, the formulation composition includes naltrexone at 40 weight percent, poly (DL-lactide) in the approximate range between 36 and 46.4 weight percent, and polycaprolactone in the approximate range between 24 and 11.6 weight percent. In addition, in order to provide anti-biofouling quality and prevent foreign body adsorption/interaction with the material of the implant, polyethylene glycol is added in a preferred content of 2.0%. The manufacturing process includes hot melt extrusion and a mini jet based implant formation stage with the optimized process space were the temperature of the process ranges from 170° C.-180° C., mixing time through the HME process ranging from 8 minutes to 12 minutes, and injection time ranging from 8 seconds to 12 seconds. The resulting implants have a uniquely shaped free of defects bio absorbable solid body.

8 Claims, 7 Drawing Sheets

(51) Int. Cl.
- *A61K 47/02* (2006.01)
- *A61K 47/10* (2017.01)
- *A61K 47/34* (2017.01)
- *B29C 45/00* (2006.01)
- B29C 45/47 (2006.01)
- B29K 67/00 (2006.01)
- B29K 71/00 (2006.01)
- B29K 105/00 (2006.01)

(52) U.S. Cl.
CPC .............. *A61K 47/10* (2013.01); *A61K 47/34* (2013.01); *B29C 45/0001* (2013.01); *B29C 45/47* (2013.01); *B29K 2067/046* (2013.01); *B29K 2071/02* (2013.01); *B29K 2105/0035* (2013.01)

(56) References Cited

U.S. PATENT DOCUMENTS

| | | | |
|---|---|---|---|
| 9,556,333 | B2 | 1/2017 | Clay |
| 2010/0003300 | A1 | 1/2010 | Markland et al. |
| 2018/0338925 | A1 | 11/2018 | Saxena et al. |

* cited by examiner

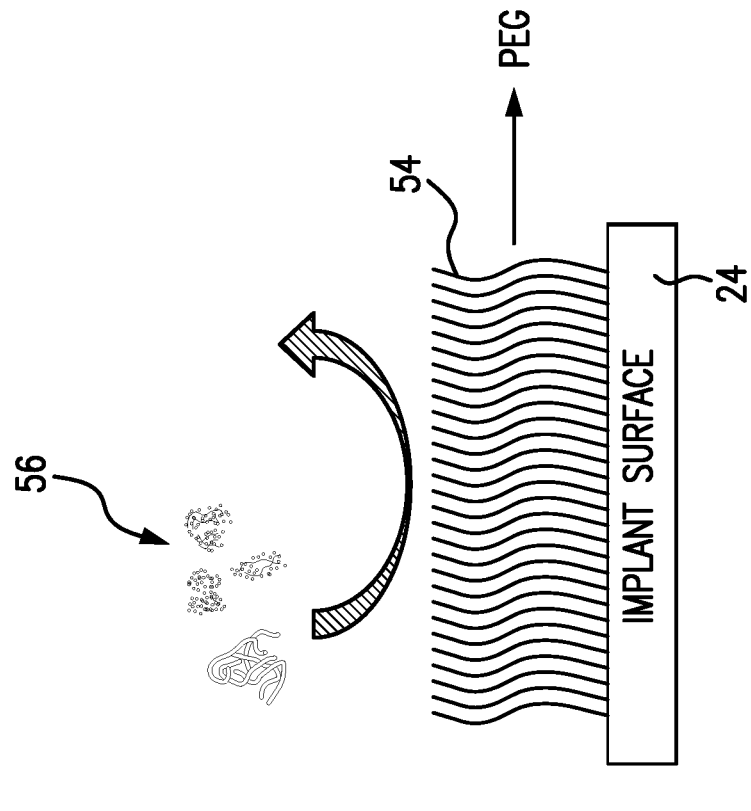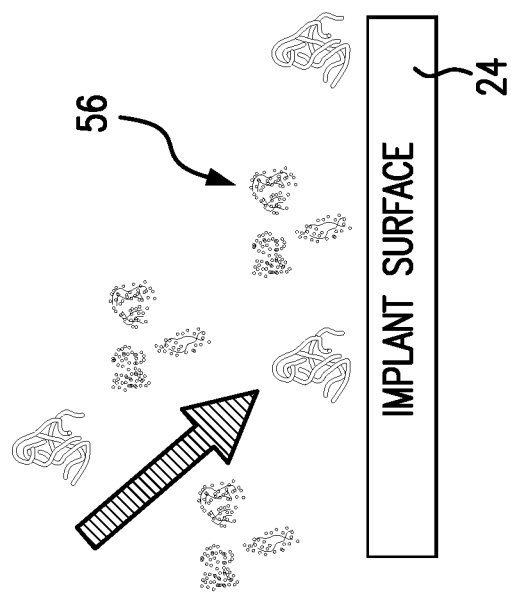
FIG. 3B
FIG. 3A

METHOD OF FABRICATING AN EXTENDED RELEASE SUBCUTANEOUS MEDICINAL DOSAGE IMPLANT SYSTEM

RELATED PATENT APPLICATIONS

This Patent Application is a Divisional Application based upon patent application Ser. No. 17/301,654, Filed on 9 Apr. 2021, now U.S. Pat. No. 11,197,819, Issued on Dec. 14, 2021.

FIELD OF THE INVENTION

In overall concept, the present invention is directed to an extended release subcutaneous medicinal dosage delivery implant which may be used as a platform providing therapeutic levels of various medications into a patient's serum and various anatomical locations of the patient's body to treat a number of medical conditions where the prolonged release of a medication is attained through the optimized composition of release controlling polymeric compounds selected for a particular medicinal agent and therapy protocol.

The present invention is further directed to a subcutaneous implant system including a drug-eluting implant which is formed from a highly homogeneous composition formulated with a medicinal agent and polymeric compounds that control the extended-release profile of the medicinal agent in a steady-state fashion.

The present invention is additionally directed to a subcutaneous implant system including a drug-eluting implant which is shaped in a specific configuration which eases the implant surgical insertion and which prevents inflammation response of surrounding tissues.

In addition, the present invention is directed to a drug-eluting subcutaneous bio absorbable implant for controlled release of a medicinal agent which egresses from the implant's outermost surface as it undergoes non-enzymatic hydrolysis of ester linkages via a combination of surface and bulk erosion over time, and which completely bio-dissolves in the patient's body, thus not requiring removal of the implant remains from the patient's body.

Furthermore, the present invention is directed to an extended release bio absorbable subcutaneous medicinal dosage delivery implant system permitting a prolonged release of a medicinal agent (with the duration of the release over an extended period of time), where the release profile and the pharmacokinetics (PK) are controlled and optimized by a specific composition and weight percentage of the implant's composition and release controlling polymeric compounds.

The present invention is also directed to a medicinal dosage delivery implant system for subcutaneous applications for treating opioid addiction where an implant includes a specific composition formulation including a medicinal agent (such as naltrexone) and polymeric release compounds such as poly (DL-Lactide) (PDL 06 0.6 dl/g) and polycaprolactone (PC 08 0.8 dl/g) in specific percentages, where the implant delivers a high serum concentration of naltrexone (3-6 ng/ml) which has been found effective in treating fentanyl addiction, and wherein after naltrexone has been completely depleted from the system, the remaining polymeric compounds continue to resorb through bio dissolution until they are naturally removed from the patient's body.

Additionally, the subject invention addresses a subcutaneous implant containing an anti-biofouling agent polyethylene glycol (PEG) to reduce (or eliminate) foreign-body adsorption/interaction at the implant surface.

Moreover, the present invention is directed to an extended release bio absorbable subcutaneous medicinal dosage delivery implant system where the visualization of the medicinal implant under the skin of the patient's body is facilitated by use of fluoroscopy to image a radio-opaque (RO) element localizer either incorporated into the body of the medication egressing implant or configured in a two-piece configuration where the bio absorbable RO elements are fabricated into an auxiliary bio absorbable implant which is fused to the main medicinal dosage delivery implant.

In addition, the present invention is directed to a method for fabrication of a subcutaneous medicinal dosage delivery implant where production of highly homogeneous (at molecular level) defect-free implants is attained through optimization of critical process parameters.

BACKGROUND OF THE INVENTION

Drug overdose deaths in the U.S. have nearly tripled from 1999-2014, surpassing deaths due to guns and motor vehicle accidents combined. Overdose is now the leading cause of accidental death in the United States. In 2017, more than 62,500 Americans died from a fatal overdose of opioids, and an estimated 2 million Americans have opioid use disorder (OUD). More recently, the influx of cheap, illicit heroin laced with fentanyl has resulted in a dramatic rise in overdose deaths. The economic impact of the opioid crisis since 2001 is estimated to be more than $1 trillion.

The number of overdose deaths (already at record levels) skyrocketed in 2020 due to the Covid-19 pandemic and its associated lockdowns. Over 81,000 drug overdose deaths occurred in the United States in the 12-months ending in May 2020, which is the highest number of overdose deaths ever recorded in a 12-month period.

It can take several months for a person to develop the necessary impulse control and skills to stay clean and sober. During recovery, an estimated 40-60% of patients experience a relapse. Consequently, the risk of accidental (and often fatal) overdose is at its highest during a relapse, because a recovering patient's tolerance is reduced after even a brief period of abstinence. Data shows high overdose death rates within four months of successfully completing 28-day opiate detoxification and rehabilitation. In one study, 91% of patients reported a relapse, 59% of which occurred within one week of sobriety, and 80% of patients relapsed within a month after discharge from a detoxification program.

Although there are effective pharmacotherapies for OUD, only a small percentage of people who would benefit from these treatments receive such pharmacotherapies. In patients who can successfully initiate therapy without an opioid agonist, naltrexone Extended Release (XR-NTX) can be effective at preventing relapse. Although buprenorphine-naloxone (BUP-NX) is a safer initial treatment for many patients than XR-NTX because of the better chance of induction, XR-NTX can decrease 24-week relapse rate to 65% among the patients who agree to treatment.

The longer a recovering addict stays in therapy, the less likely they are to relapse. Recovering addicts need time to adjust their lifestyles, to integrate into supportive social services, and to allow their physiology to recover from the opioid abuse. There is an unmet need for effective pharmacological therapy of opioid use disorder that requires less than monthly treatment. A substantial number of medical professionals believe that if there was available a version of naltrexone that lasted for 6 months, such would lead to a great advantage in saving lives.

In this context, bio absorbable polymeric drug delivery devices have potential to revolutionize the treatment of many chronic medical conditions, and specifically, the opioid use disorder.

Thus, it would be highly desirable to provide an effective long-term pharmacological therapy of opioid use disorder, which provides a long-duration (6 months or even longer than a year) therapy where a medicinal agent, for example, an opioid agonist (such as for example, naltrexone base anhydrous) could be safely released into a patient's body over a long period of time with a controlled release profile.

It also would be highly desirable to provide a treatment protocol based on a release of a medicinal agent into a patient's body by a subcutaneous extended release medicinal dosage delivery implant system insertable into a patient's body for controlled delivery of a medicinal agent (for example, the opioid agonist naltrexone base anhydrous) in a predetermined release profile over an extended period of time which is fully bioabsorbable.

In addition, it would be highly desirable to provide a drug-delivery device composed of safe compounds, such as, for example, the release polymers (excipients) including polycaprolactone) (PC08 0.8 dl/g) and Poly (DL-lactide (PDL06 0.6 dl/g) combinations are selected based upon their effectiveness safety considerations. These polymers have been the subject of numerous publications, received FDA approval and/or CE Mark registration, and a number of medical and drug-delivery devices have been used clinically which contain one or both of these excipients.

Polycaprolactone (PC08 0.8 dl/g) is a well-tolerated bio-degradable and bioresorbable polymer that is attractive for long-term drug delivery. It was synthesized in the early 1930s by van Natta using "ring opening polymerization" to create ε-caprolactone. Polycaprolactone is a semi crystalline aliphatic polyester with a low glass transition temperature and melting point (59-64° C.). It is hydrophobic and is ideal for extended drug delivery because of its high permeability to many drugs, good biocompatibility, and it has slow rate of bio resorption in biological systems.

Polycaprolactone is completely biodegradable and bioresorbable. Degradation studies have established that polycaprolactone is biodegraded in a two-step process. The first stage involves surface erosion and bulk degradation. It is facilitated by the non-enzymatic hydrolytic cleavage of the ester bonds throughout the entire polymer matrix and obeys first-order reaction kinetics.

With surface erosion, the hydrolytic cleavage of the polymer complex only occurs at the surface of the implant. This releases oligomers and carboxyl groups into the surrounding tissue.

Bulk degradation occurs when water is able to penetrate into the core of the implant causing random scissions that allow the inner oligomers to diffuse external the implant, resulting in the loss of weight and bulk of the implant.

The second stage occurs when smaller fragments of the polycaprolactone polymer (<3000 g/mol) are hydrolyzed and are free to diffuse from the core of the implant. These smaller oligomers are taken up by macrophages, giant cells and fibroblasts—where they undergo intracellular degradation.

The first approved biomedical devices containing oly-caprolactone were sutures using monocryl which is a copolymer of ε-caprolactone and glycolide (25/75). It has been in use since receiving FDA approval in 1995 (Ethicon Inc., Somerville, NJ). Other sutures containing polycaprolactone in clinical use include StrataFix™ Spiral PGA-PCL (Ethicon Inc., Somerville, NJ), Redicaprone 25™ (Myco Medical, Apex, NC) and Quill™ Monoderm™ (Surgical Specialities, Wyomissing, PA).

Other FDA-approved and products in development containing polycaprolactone include Artelon®, Urolon®, Caprenor®, Resilon™, polycaprolactone artificial tracheal implanted in child and adults, and PCL drug-eluting stent (Ha D H, Kim J Y, et. al).

In 2006, Sun et. al. looked at the long-term degradation of polycaprolactone in rats for a period of 3 years. They studied the distribution, absorption and excretion of polycaprolactone capsules with a MW of 66,000 g/mol using radioactive labeling. The mono polymeric polycaprolactone capsules required 30 months to breakdown into low MW fragments (8000 g/mol). The same authors implanted trititum-labeled polycaprolactone (MW=3000 g/mol) in rats. The first radioactive tracer was detected in the plasma at 15 days. The radiolabeled metabolites were recovered from the rodent's urine and feces. 92% of the radioactive tracer was excreted into the urine and feces at 135 days. The degradation of polycaprolactone occurs via hydrolysis. Polycaprolactone→6-hydroxycaproic acid→Acetyl-CoA→Citric acid cycle→$CO_2$+$H_2O$.

Pulkkinen et. al. evaluated 2,2-bis(2-oxazoline) linked polycaprolactone (PCL-O) in a rodent model. They evaluated the hematology, clinical chemistry, histopathology of the local implantation site and the major organs (e.g. heart, lung, liver, kidney, spleen and brain) at 3 months after implantation. They concluded that PCL-O was biocompatible and safe.

As a mono polymeric compound, polycaprolactone requires 2-4 years to completely degrade. Co-polymerization with lactides or glycolides can dramatically speed up the rate of hydrolysis and biodegradation. Co-polymeric polycaprolactone blends can be tuned to achieve the ideal degradation kinetics for a given medical device or drug-delivery system.

One example of a successful and well-tolerated copolymeric blend is poly (DL-lactide) and ε-caprolactone, which is currently approved and used as a nerve guide. In 1996, Dunnen et. al., concluded that the use a biodegradable nerve guide constructed of a copolymer of DL-lactide and epsilon-caprolactone was superior to autologous nerve grafts for the repair of short nerve gap (1 cm) in a transected peripheral nerve.

In 2003, Pego et. al. used a polycaprolactone based copolymer as one of the candidate formulations to create a bioresorbable nerve guide. They implanted polymer films made of poly (1,3-trimethylene carbonate) (TMC) and copolymeric blends of TMC with either 52 mol % D, L-lactide (DLLA) or 89 mol % PCL into the subcutaneous space of rats for periods up to one year. The pure TMC films completely resorbed in less than one year. The TMC copolymers degraded at a occurred at a much slower rate. The TMC-DLLA copolymer lasted longer but was still resorbed 20 times faster than the TMC-PCL formulation. The TMC-PCL copolymer had the longest duration. Histopathologically, an acute inflammatory tissue reaction was noted after the implantation procedure. Later a mild macrophage-mediated foreign body reaction and fibrous encapsulation was noted as the polymer resorbed. This study demonstrated that TMC and both TMC copolymers (TMC-DLLA and TMC-PCL) were biodegradable and biocompatible materials.

In the commercial development of the nerve guide (Neurolac®), the TMC was completely dropped and a copolymeric blend of poly (DL-lactide) and poly (ε-caprolactone)

was selected to fabricate the conduit to protect the peripheral nerve during regeneration after injury. Neurolac® received FDA approval via the 510 (k) pathways in 2003. "Biocompatibility, mechanical and physical property testing, in vitro degradation testing, and performance testing in an animal model provide reasonable scientific evidence that Neurolac® nerve guide is substantially equivalent to the predicate devices."

The Neurolac® Nerve Guide is used in Neural Engineering as a protective conduit to facilitate the repair of a transected peripheral nerve which is a tube made of a copolymeric blend of PDDLA and PCL (65/35). This has been used for reconstruction of a peripheral nerve discontinuity and provides guidance and protection to regenerated axons and prevents ingrowth of fibrous tissue into the nerve gap during nerve regeneration from the proximal to the distal nerve stump of the transected nerve. Degradation of the Neurolac® Nerve Guide occurs through hydrolysis leading to gradual reduction of molecular weight with initial mechanical properties being retained up to 10 weeks providing support and protection to the healing nerve whereafter, rapid loss of mechanical strength and gradual mass loss has been found. The final degradation products, lactic acid and hydroxyhexanoic acid, are resorbed, metabolized and excreted by the body and studies show that the Neurolac® Nerve Guide has been resorbed within 16 months.

Ellans' e®, (Sinclair Pharma, London, UK) is a PCL Dermal Filler/Collagen Stimulator that received CE marking in 2009 (Class III medical device) for the aesthetic correction of facial wrinkles, folds and hand rejuvenation by deep dermal and subdermal injection/implantation of the product. Ellans' e® is a suspension of PCL microspheres (30% by volume) in a carboxymethyl cellulose gel carrier. The typical volume for facial injection is ~2 ml.

After a decade of clinical use in the subdermal space, Ellans' e®, has been proven both safe and effective. From 2009 through 2017, >600,000 syringes were used. In terms of safety, a post-market surveillance (PMS) study found only 355 adverse events out of >600,000 uses (an adverse rate of 0.056%) during this period. In terms of efficacy, 40 patients were evaluated who had received a subdermal injection of the PCL—Ellans' e® gel for the treatment of nasolabial folds. At the end of 12 months there was >90% improvement in the Global Aesthetic Improvement Scale and at 2 years patient satisfaction was rated as "high" in 70-80% of the patients, thus confirming a longer duration of action than a hyaluronic acid filler. By 2020, 3 years after the PMS was completed, more than 1 million syringes have injected with the same low adverse event rate and high efficacy.

In the tissue/Bone Engineering, Osteopore™ manufactures customized, bioresorbable 3D-printed implants made of poly (ε-caprolactone) that are used as a bone filler to fill defects caused by trauma or surgery. These implants are used in orthopedic, neurosurgery and maxillofacial surgery. The PCL scaffolding provides immediate load-bearing tectonic support (similar to trabecular bone) and later facilitates bone regeneration as the PCL is slowly resorbed and replaced with autologous bone. The development of this technology was initiated in 1996. The first-in-human application of this technology was implantation of a 3D-printed burr hole cover in 2002. US FDA approval (510(K)) occurred in 2006 for a bone void filler and CE marking for the "osteoplug" burr hole cover and the "osteomesh" for orbital floor reconstruction (50×50×1 mm sheets) occurred in 2009. The 2006 510(k) summary of substantial equivalence states that, "The Osteopore PCL Scaffold™ shares the same material biocompatibility, cytotoxicity, genotoxicity, sensitization, chronic toxicity and carcinogenicity as FDA cleared suture products. Osteopore scaffolds are made initially from filaments which are equivalent to FDA cleared suture devices".

From 2006-2018, Osteopore implants were implanted in >20,000 surgeries. A recent report evaluated the 10-year outcomes of 174 patients who had a total of 275 PCL burr hole cover implants inserted between 1 Apr. 2006 and 31 Sep. 2015. The PCL implants were well tolerated and were not associated with a higher-than-expected rate of surgical complications. There were no reports of infection originating from the implants.

A Mesofol® surgical sheet (Biomet, Inc, Warsaw, IN) is used to reinforce and repair incompetent soft tissue defects that are encountered during the surgical repair of a hernia or a fascial defect. Each sheet is made from a lactide-caprolactone copolymer. The largest available sheet measures 20 cm×25 cm×40 μm. The Mesofol® Surgical Sheet received FDA approval by a 510(k) pathway in 2007 and is found to be chemically broken down by hydrolytic cleavage of the polymer, giving rise to three monomers: 6-hydroxycaproic acid, D-lactic acid, and L-lactic acid. 6-hydroxycaproic acid is broken down to acetyl-CoA units via β-oxidation (fatty acid metabolism) for further degradation via the Krebs cycle. L-Lactate is broken down in the lactic acid cycle to glucose via pyruvate. These two monomers are thus degraded to products that are physiologically metabolized by the body.

Naltrexone base anhydrous is qualified as an opioid antagonist and is used for treating opioid addiction problems. Numerous implantable tablets containing naltrexone and some biodegradable polymers are currently on the market. There are over 20 approved devices that use poly (DL-lactide) or a related stereo-isomer lactide compound alone, or as a copolymer. For example, Vivitrol (produced by Alkermes) uses naltrexone in PLGA microspheres. Another version of implants of naltrexone has been developed by Dr. G. O'Neill which includes naltrexone embedded in a matrix of biodegradable polymer microspheres. The composition of O'Neill implant comprises approximately 50% naltrexone, 49% of biodegradable polymer, and less than 1% of magnesium stearate. These implants are normally inserted under antibiotic prophylactics. After preparing these implants, they need to be sterilized prior to packing. The utilization at high temperature at high gamma radiation results in chemical degradation. Unfortunately, degradation of Dr. O'Neill's implant is toxic in nature and therefore the contents of naltrexone are to be minimized to eliminate the side effects of these implants.

Other naltrexone implantable tablets, such as naltrexone embedded in magnesium stearate complex (WO1998030171 by L. L. Gooberman), or naltrexone implant developed by G. Cherman at Towne Pharmacy, New Jersey, or the implant of naltrexone developed by Dr. G. O'Neill of GO-Medical Industries, may cause irritation and inflammation at the site of the implantation when combined with naltrexone in implantable tablets, which limit their use, and cause the problem of toxic degradation product noroxymorphone.

As one of the examples of implantable naltrexone tablets, PCT Application PCT/IN2016/050280 (invented by N. Saxena, et al.) discloses naltrexone implantable tablets which are devoid of metal salts and corticosteroids, and which provide consistent and controlled amount of naltrexone for three months or more. These implantable naltrexone tablets resolve the issues associated with magnesium salt, triamcinolone and noroxymorphone generated by the utilization with higher gamma radiation of previous naltrexone tablets which are implantable in a patient's body. Such naltrexone implantable tablet composition comprises naltrexone embedded in one or more biodegradable co-polymers or polyesters. In certain embodiments, the biodegradable polymers/polyester comprises one or more DL-lactides/glycolide copolymers in weight % such as 50:50, 65:35, 75:25, 85:15, 5:95, 15:85, and 25:75. The content of 50:50 DL-lactide/glycolide copolymer is preferred.

After making the implant, these implants are put into polypropylene syringes and packed in a heat sealable serializable pouch which is subjected to ethylene oxide sterilization. As ethylene oxide cannot penetrate metal/polymeric film pouches, aluminum pouches are not used as the final packaging material. The packed implants are subjected to radiation, which is more preferable than ethylene oxide sterilization. The gamma radiation is kept at intensity 8 to 25 kgy, preferably 8-12 kgy so as to reduce the neuroxymorphone degradation and yet maintaining the sterility of the product. Each naltrexone implantable tablet preferably combines nltrexone in the amount of 500-2000 Mg embedded in the biodegradable polymers/polyesters.

The present implant system is a further development in the field of subcutaneous medicinal dosage delivery implants which is optimized for better controllability of medicine release profile, length of treatment, configuration and homogeneity of the implant, and optimization of fabrication process.

SUMMARY OF THE INVENTION

It is therefore an object of the present invention to provide a subcutaneous implant system platform designed to control the release of therapeutic levels of various medicinal agents/biological compounds into the patient's serum and various anatomical locations of the patient's body for effective treatment of a number of medical conditions.

It is another object of the present invention to provide an extended release bioabsorbable subcutaneous medicinal dosage delivery implant system implantable beneath the skin of a patient for releasing a medicinal agent over an extended period of time in a controlled fashion for the purpose of treating a number of medical conditions.

It is a further object of the present invention to provide a subcutaneous medicinal dosage delivery implant system fabricated with a drug-eluting bio absorbable disk-shaped solid implant comprised of a medicinal agent in combination with polymeric release controlling compounds to control the delivery of the medicinal agent in a steady-state fashion with a desired release profile over a prolonged period of time, such as, for example, 6 months-up to and over 1 year, where the rate of release of the medicinal agent is controlled by varying the weight percentages and composition of the release controlling polymers in order to either slow down or accelerate the pharmacokinetics (PK) as needed for a treatment protocol.

In addition, it is an object of the present invention to provide a subcutaneous implant system where the implant composition has anti-fouling properties for preventing foreign body interaction.

Another object of the present invention is to provide subcutaneous medicinal dosage delivery implant where the medicinal agent egresses from the implant's outermost surface while it undergoes non-enzymatic hydrolysis of ester linkages via a combination of surface and bulk erosion over time, and where, once the medicinal agent has been completely depleted, the remaining polymeric compounds continue to resorb through biodissolution until they are naturally removed from the body.

It is an additional object of the present invention to provide a subcutaneous medicinal dosage delivery implant system where the implant visualization inside the body of the patient is facilitated by radiopaque localizing elements incorporated into the implant (in one- or two-piece configuration), which are bio absorbable and selected for their safety biocompatibility.

Still another object of the present invention is to provide a method of fabricating the extended release bioabsorbable subcutaneous medicinal dosage delivery implant system where the shape of the implant is optimized to prevent inflammation of tissues under the patient's skin, where the medicinal agent's release profile is controlled and optimized by a specific composition of the polymeric release controlling compounds and their relative weight percentage, and where the manufacturing process is optimized to attain manufacturing process conditions (temperature, mixing time, and injection time) which prevent formation of inhomogeneous implants or their degradation.

It is an additional object of the present invention to provide a completely bioabsorbable subcutaneous medicine dosage delivery implant system with implants having a unique design with smooth surface and edges to avoid any possible inflammatory responses, where the unique manufacturing process results in high quality homogeneous implants free of unwanted degradation of the material of the solid implant which has a unique product composition specifically formulated for the prolonged medication release profile with a serum level of naltrexone sufficient to fight the effect of fentanyl which may present in heroin.

In one aspect, the present invention is directed to an extended release bio absorbable subcutaneous medicinal dosage delivery implant system including at least one bio absorbable implant having a solid implant body. The solid implant body is formed from a material having a composition formulated with at least one medicinal agent and release controlling polymeric compounds intermixed substantially homogeneously with the medicinal agent in a predetermined weight relationship to one another. The release controlling polymeric compounds control the release profile of the medicinal agent for an extended time period in accordance with a desired treatment protocol.

The release controlling polymeric compounds may include at least poly (DL Lactide) (PDL 0.6 dl/g) in a weight % ranging from 6% to 52.2% and polycaprolactone (PC 0.8 dl/g) in a weight % ranging from 5.8% to 51%.

The material of the solid implant body may further include an anti-biofouling agent containing polyethylene glycol (PEG) homogeneously intermixed with the medicinal agent and the release controlling polymeric compounds. A weight % of the anti-fouling agent may preferably be about 2%.

In one application, for example, for treatment of opioid use disease, the medicinal agent may preferably include naltrexone base anhydrous (naltrexone) having a weight % of about 40%.

In a preferred embodiment, the composition of the material of the implant body may include 40% of naltrexone, 36% of poly (DL-lactide) PDL 0.6 dl/g, and 24% of polycaprolactone PC 0.8 dl/g.

In another preferred embodiment, the composition of the material of the implant body may include 40% of naltrexone, 46.4% of Poly (DL-lactide) PDL 0.6 dl/g, 11.6% of polycaprolactone PC 0.8 dl/g, and 2% of polyethylene glycol (PEG).

The subject implant is designed to deliver high serum levels (3-6 ng/ml) of naltrexone to increase efficacy against fentanyl which may present in heroin, The implant may further include a radiopaque localizer embedded in the implant body. Alternatively, the implant may further include an auxiliary implant body containing a radiopaque localizer and fused with the medicinal agent releasing implant body.

The radiopaque localizer may be fabricated from a material selected from a group of iron oxide, gadolinium, barium sulfate, Iohexol, bismuth sub-carbonate, bismuth oxychloride, and their combinations.

The implant body is a solid implant body having a predetermined asymmetric configuration with a smooth surface devoid of sharp areas to prevent an inflammatory response of the patient's tissues to the implant remaining in the body.

In another aspect, the present invention is directed to a method of fabricating the extended-release bio absorbable subcutaneous medicinal dosage delivery implant system which comprises the following steps:

mixing at least one medicinal agent at a first temperature of 176° C.+/−5° C. and release controlling polymeric compounds at a second temperature 176° C.+/−5° C. in a feeder to form an injection mixture, and injecting the injection mixture into a segmented screw extruder having a first plurality of heating zones and a second plurality of mixing zones, each mixing zone creating a specific predetermined shear rate and a process boundary.

The method continues by actuating the segmented screw extruder, and passing the injection mixture along the actuated segmented screw extruder from its input to its output during a mixing time ranging from 8 min to 12 min.

During passage of the injection mixture along the actuated segmented screw, the injection mixture is exposed to a temperature regime ranging from 170° C. to 180° C., while passing through the first plurality of heating zones, thus forming a melted homogenous injection mixture.

The subject method further continues installing a mini-jet implant formation unit at the output of said segmented screw extruder, passing the melted homogeneous injection mixture to the mini-jet implant formation unit and forming the implants therein for a duration of about 8 sec-12 sec, to result in a highly homogeneous solid defect-free implant.

The subject matter further comprises the step of forming the solid implant body having a smooth surface devoid of sharp areas.

In the subject method, the step of forming the injection mixture in the feeder further includes the step of adding the plasticizer and anti-fouling agent containing polyethylene glycol (PEG) to the medicinal agent and the release controlling polymeric compounds in the feeder.

In the method, the medicinal agent may include naltrexone base anhydrous.

The subject method further includes forming the injection mixture from the release controlling polymeric compounds which may include at least pPoly (DL-Lactide) PDL 0.6 dl/g in a weight % ranging from 6% to 52.2%, and polycaprolactone PC 0.8 dl/g in a weight % ranging from 5.8% to 51%.

In one preferred embodiment, the injection mixture is formed by mixing 40 weight % of naltrexone base anhydrous, 36 weight % of poly (DL-lactide) PDL 0.6 dl/g, and 24 weight % of polycaprolactone PC 0.8 dl/g.

In another preferred embodiment, the injection mixture is formed by mixing 40 weight % of naltrexone base anhydrous, 46.4 weight % of Poly (DL-lactide) PDL 0.6 dl/g, 11.6 weight % of polycaprolactone PC 0.8 dl/g, and 2 weight % of polyethylene glycol (PEG).

These and other objects of the present invention and the advantages thereof will become apparent in view of the further detailed description when taken in conjunction with the accompanying Patent Drawings.

BRIEF DESCRIPTION OF THE DRAWINGS

FIGS. 3A-3B illustrate the concept of the bio-fouling property in the present implant with FIG. 3A showing the foreign body absorption-interaction with the implant surface, and FIG. 3B showing the PEG compound preventing the foreign body absorption—interaction with the implant surface;

DESCRIPTION OF THE PREFERRED EMBODIMENTS

Figure 1A:
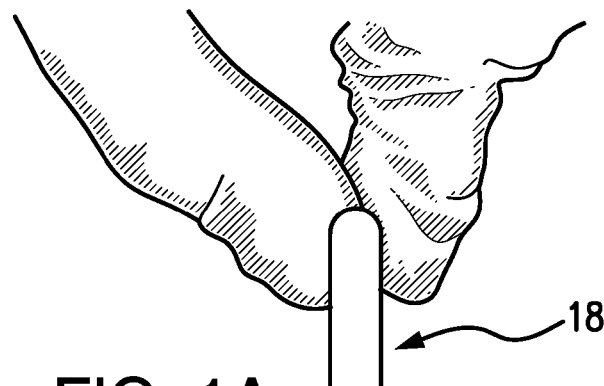
FIGS. 1A-1B are representative of the subject implant system surgically inserted under the skin of a patient's body.

The present subcutaneous implantable medicinal dosage delivery implant system for the extended release of medicinal agent is a further development for releasing of a medication over an extended period of time for the purpose of treating numerous medical conditions, where pharmacokinetics is controlled by varying the weight percentages of the release controlling polymers, which is enhanced by embedding radiopaque localizer elements in the implant, and where the implant contains an anti-fouling agent to prevent foreign-body absorption/interaction with the implant surface. The subject implant is fabricated by a combination of hot melt extrusion and injection molding where the unique process design space (temperature regime, mixing time regime, and ejection time regime) has been found to provide highly homogeneous implants which are free of defects.

The present invention embraces, in its broad sense, an extended-release subcutaneous medicinal dosage delivery implant platform designed to provide therapeutic levels of numerous medications into the patient's serum and various locations of the patient's body for the purposes of treating a number of medical conditions.

As an example only, but not to limit the scope of the subject invention to a particular application, the following description will address the BIOPIN, i.e., Biodegradable Polymeric Implant containing naltrexone base anhydrous (NTX) adapted for treating opioid use disorder. It is however to be understood that this is only an exemplary embodiment of the subject system, and medicinal agents other than naltrexone, and other therapy protocols for treating numerous medical conditions are contemplated.

The present Biodegradable Polymeric Implant Containing naltrexone base anhydrous (BIOPIN) may be a 6-12 month (or longer) subcutaneous bio absorbable implant for the prevention of relapse to opioid dependence, following opioid detoxification and alcohol use disorder. The BIOPIN implant includes two essential components: a medicinal agent naltrexone base anhydrous (NTX) and a combination of polymer compounds. The polymer compounds are selected to regulate passive release of the medicinal agent, and are formulated using at least poly (DL-lactide) PDL 0.6 dl/g, and polycaprolactone PC 0.8 dl/g or PC 0.4 dL/g.

The BIOPIN is a solid implant containing 40 wt. percent naltrexone base anhydrous (NTX) and 60 wt. percent release controlling polymers. The release-controlling polymers are comprised of poly-(DL lactide) (range 6 wt. %-52.2 wt. %) and polycaprolactone (range 5 wt. %-51 wt. %). Small amounts (2 wt. %) of the plasticizer, polyethylene glycol (PEG), can also be added to extend the duration of NTX release and to act as an anti-fouling agent.

Polycaprolactone is degraded through the hydrolytic cleavage of ester groups under physiological conditions, thus it is attractive as an implantable biomaterial. Polycaprolactone undergoes a non-enzymatic hydrolysis of ester linkages, which is attributed to random chain scissions, causing a characteristic erosion, confirmed by the decrease in molecular weight.

The main mechanism of Poly (DL-lactide) degradation is the hydrolysis of the ester bond backbone. The amorphous character of poly (DL-lactide) suggests faster degradation than the other poly lactic acids. The degradation products are lactic acid or lactic acid oligomers. The degradation is thought to be catalyzed by the newly formed terminal carboxylic acid groups at the ends of the PLA chains which can cause the polymer to swell as degradation proceeds (Bode, et al. 2019).

In the pre-clinical studies, the proposed human dose was determined based on rodent and canine PK studies. The dosages tested in the rat study were 320 mg, 640 mg, and 1280 mg NTX per 260-gram animal. The dosages tested in the canine study were 600 mg and 1200 mg per 10 kg animal. The planned dose in humans is 8 grams of NTX. The dose of NTX is not adjusted for the weight of the human subject. The implant is intended to be placed into the subcutaneous space of patients with Opioid Use Disorder (OUD) to prevent relapse following detoxification. The bio-resorbable implant does not have to be removed surgically, however, in cases of a medical emergency, removal can be effected. For this, fluoroscopic visualization of the implant is needed which can be provided by radio-opaque elements embedded in the implant. Those may be in the form of radio-opaque, bio absorbable compounds including iron oxide, gadolinium, barium sulfate, Iohexol, bismuth subcarbonate, bismuth oxychloride, and combinations.

BIOPIN is expected to release adequate levels of naltrexone for six to twelve months, which can be assessed in individual patients by measuring NTX drug levels in serum.

Almost all of illegally sourced heroin contains some fentanyl. Thus, there is a need for newer XR-NTX to release higher serum NTX concentrations than the currently available XR naltrexone compositions. In order to attain potential efficacy against fentanyl, the subject BIOPIN has been designed to deliver higher serum levels of NTX (3-6 ng/ml) throughout its therapeutic lifespan. The use of the BIOPIN implant reduces the incidence of fentanyl-induced respiratory depression and death.

Referring to FIGS. 1A-1B and 2A-2D, the present system 10 constitutes a platform designed to provide therapeutic levels of various medications delivered into the patient's serum, entire body, or various anatomical locations in the patient's body, for an extended period of time as required by specific therapy protocols to treat medical conditions.

Figure 1B:
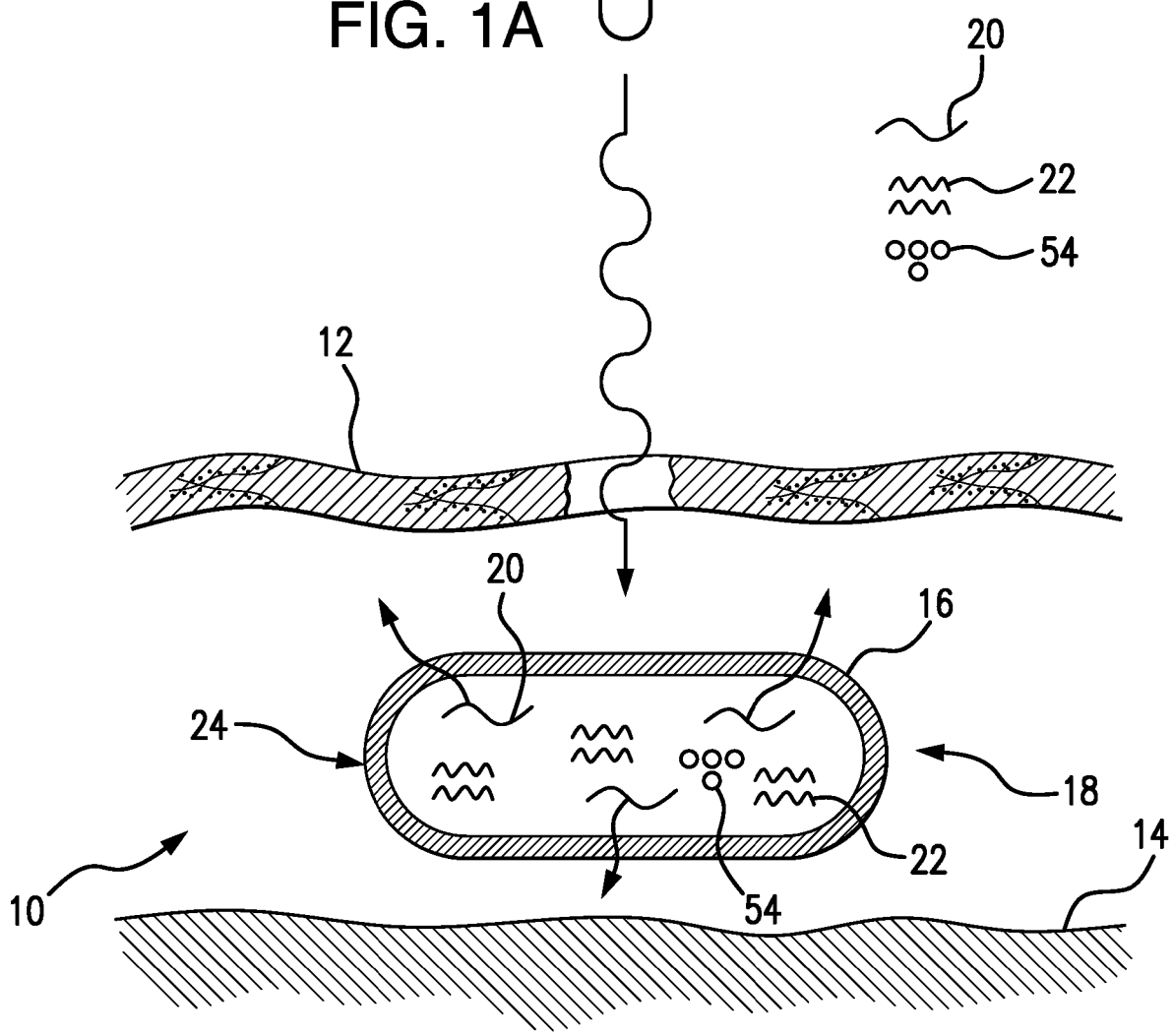

Referring to FIGS. 1A-1B, the subject extended release subcutaneous medicinal dosage delivery implant system 10 is implanted beneath the skin of a patient by a preferred number of surgical procedures at anatomical locations required by the treatment protocol with the intention of releasing a medication over an extended period of time (sometimes over 12 months) for the purpose of treating a number of medical conditions (diseases).

As presented in FIGS. 1A-1B and 2A-2D, the subject system 10 includes at least one implant 18 for being implanted under the skin 12 of a patient 14 under treatment. The implant 18 is the drug-eluting unit which has a solid disk-shaped bio-absorbable body 16 formed from a composition which comprises one or several medicinal agent(s) 20 and a composition of polymeric compounds 22. The polymeric compounds 22 in the present composition are formulated which are homogeneously intermixed and melted together with the medicinal agent 20 to form the chemical composition of the implant body 16 to control the release of the medicinal agent 20 from the implant body 16 in a steady-state controlled manner into the patient's body.

Once the implant 18 is implanted under the skin 12 of the patient 14, the medicinal agent 20 (triggered by the physiological conditions in the surrounding tissues) egresses from the implant's outermost surface 24 as a result of non-enzymatic hydrolysis of ester linkages between the medicinal agent 20 and the release controlling polymeric compounds 22 via a combination of the surface and the bulk erosion over time.

After the medicinal agent 20 has been completely depleted, the remaining polymeric release compounds 22 in the implant body 16 continue to resorb through bio dissolution until they are naturally removed from the patient's body. The subject implant 18 does not have to be removed by a surgical procedure, as it is completely bio absorbable in the patient's body.

Although the present system is applicable for treating various medical conditions with various medicinal agents released into the patient's body, as one of the examples (but not to limit the scope of protection for this particular application), the subject system will be further described for treatment of opioid dependency treatment. In this particular application, as an example, the medicinal agent 20 in the implant 18 may include a naltrexone base anhydrous, further referred to herein as naltrexone. The subject system will be also further referred to herein intermittently as a BIOPIN, e.g., Biodegradable Polymeric Implant containing naltrexone (NTX).

Being implanted under the skin 12 of the patient body 14, the subject BIOPIN implant 18 releases the medicinal agent (naltrexone) with the rate (or the release profile), which is controlled by a specific combination of the release controlling polymers 22 and their percentages in each implant 18.

A specific composition for the implant 18 has been developed to control the pharmacokinetics (PK) of the solid extended-release subcutaneous medicinal dosage implant 18. This composition may be varied to either slow down or to accelerate the PK as needed for each particular treatment protocol.

The medicinal agent, i.e., naltrexone, is evenly distributed within the implant body 16 and all ingredients of the composition of the implant body 16 are highly homogeneously intermixed with one another.

As presented in FIGS. 2A-2D, the implant 18 is fabricated in a somewhat asymmetric configuration of the implant body 16. The implant body 16 may have a planar disk-like configuration. The implant body 16 may have planar or somewhat slightly curved convex sides 32 and 34 joined at a periphery thereof by smooth curved edges 36 extending along the entire perimeter of the convex sides 32, 34. The curved edge 36 of the implant body 16, as well as the entire surface thereof, is devoid of sharp edges. Completely smooth outer surface of the implant body 16 devoid of sharp edges helps to minimize (or avoid) possible trauma to surrounding tissues, thus dramatically decreasing (or eliminating) an inflammation response of the patient's body to the implant 18 embedded under the skin of the patient's body.

Figure 2A:
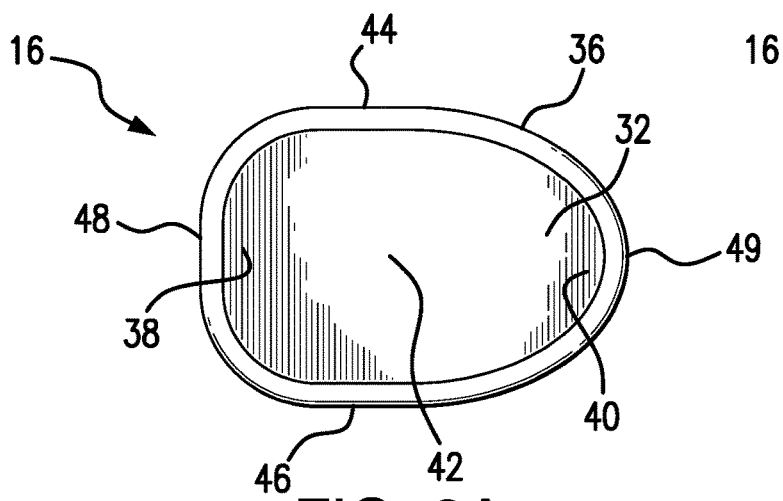
FIGS. 2A-2D are representative of the subject system's bioabsorbable subcutaneous implant with FIG. 2A being a planar view, FIG. 2B being a side view, FIG. 2C being a perspective view of the implant with the embedded OR localizer element, and FIG. 2D showing an alternative design of the implant in a two-piece implementation.
Figure 2B:
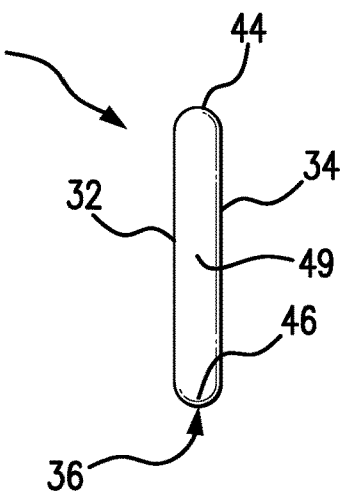

Each side 32, 34 of the implant 18 has a wider end portion 38, and a narrow end portion 40 interconnected by a central portion 42. As an example, the wide end portion 38 may have the width of about 4.55 mm. The side portions 44 and 46 of the curved edge 36 are joined at the wide end portion 38 by the end perimeter portion 48 in a smooth arcuate configuration with a radius of approximately 1.82 mm. The side perimeter portions 44 and 46 are connected at the narrow end portion 40, by a smooth arcuate portion 49. As shown in FIG. 2B, the thickness of the curved edge 36 is approximately 0.64 mm with the radius of approximately 0.32 mm.

The combination of the outer surface/edges smoothness with the asymmetric configuration of the implant 18 (with the wide end portion 38 and narrow end portion 40), and the slightly convex (almost planar) shape of the sides 32 and 34 of the implant body 16 provide a convenient arrangement for maneuvering of the implant 18 into the patient's body with a minimal traumatism during the insertion surgical procedure.

The unique implant configuration allows for in-vitro release data modeling and more accurate IV-IVC (in-vitro in-vivo correlation) which is helpful in prediction of the in-vivo performance of a drug based on the in-vitro drug release profiles. Various equations modeling the dissolution of the drugs are known which compute the in-vivo absorption of drugs.

Figure 2C:
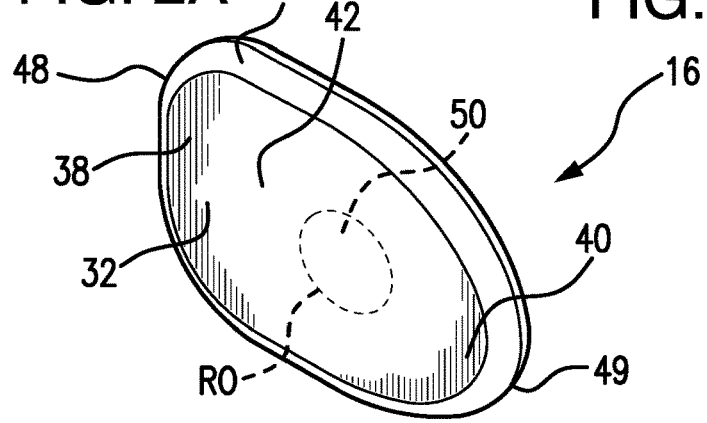
Figure 2D:
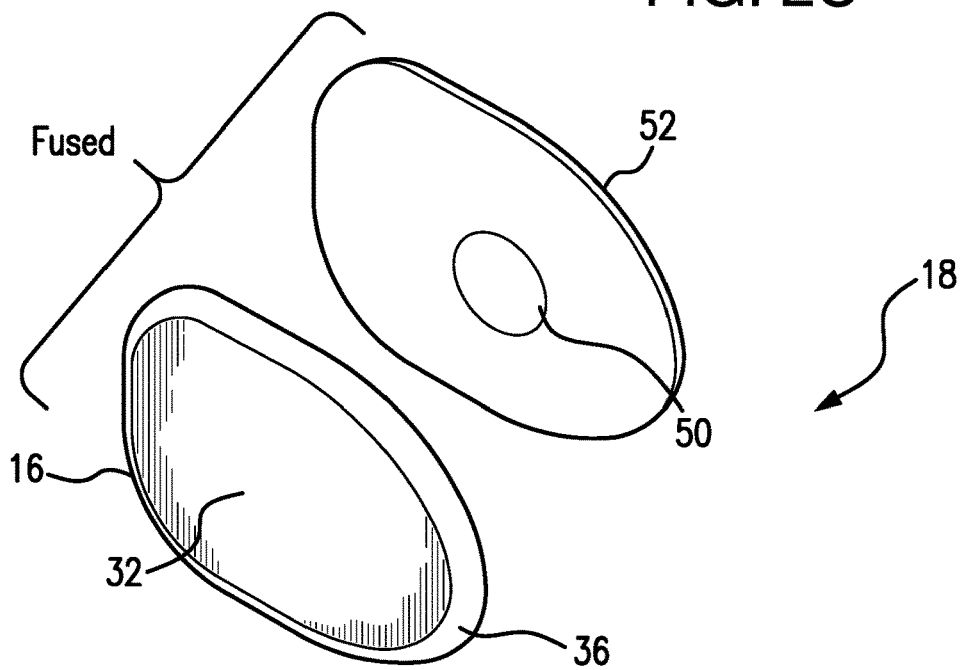

The present implant 18 is completely bio dissolvable at the end of the treatment period and does not need to be surgically removed. However, in the event of a medical emergency (such as, for example, intolerance to the medication or to the protocol of medicinal agent release), the implant 18 must be surgically removed. To facilitate the surgical removal of the implant, visualization of the medical implant is needed and usually provided by using fluoroscopy. In order to facilitate the visualization of the implant position under the skin of a patient, a radiopaque (RO) localizer element 50 may be embedded into the implant body 16. The RO component 50 may be fabricated using either a one-piece, integrated design (as shown in FIG. 2C), or as a two-piece design (shown in FIG. 2D) with the bio absorbable RO element(s) 50 fabricated into a separate bio absorbable auxiliary implant 52 which is fused to the main medicinal dosage delivery implant body 16. In any implementation, the RO elements 50 are bio absorbable and are selected for their safety by compatibility.

Being incorporated into the solid formulation of the implant 18, the medicinal agent (for example, naltrexone) and the release controlling polymers, such as poly (DL-lactide) (PDL), and polycaprolactone (PCL), as well as the plasticizer/anti-biofouling agent polyethylene glycol (PEG), are GRAS (generally recognized as safe materials) category materials.

One of the unique features of the subject formulation composition of the solid implant 18 is the combination of naltrexone and the release controlling polymers including poly (DL-lactide) (PDL) and polycaprolactone (PCL) in specific weight percentage shown in Tables 1 and 2. The poly (DL-lactide) is an ingredient which slows the release of the medicinal agent, while polycaprolactone is an ingredient which accelerates the release. The unique weight percentage of the relationship between these two polymer compounds (in relation to the medicinal agent) provides a control over the release profile for a particular treatment protocol. In Tables 1 and 2, the BIOPIN-6 compositions were formulated by increasing the polycaprolactone content, and the BIOPIN-8 compositions were formulated by increasing the poly (DL-lactide) content.

The BIOPIN compositions presented in Table 1 and 2 contain about 40 wt. % of naltrexone base anhydrous, which provides delivery of an increased serum level of NTX (3-6 ng/ml) throughout the therapeutic lifespan of the BIOPIN-8 to attain efficacy against fentanyl.

TABLE 1

| | BIOPIN-7 Composition | | | | |
|---|---|---|---|---|---|
| Composition | BIOPIN-6 | B7-1 | B7-2 | B7-3 | B7-3 w/o Iron Oxide |
| naltrexone | 40% | 40% | 40% | 40% | 40% |
| poly(DL-lactide) | 36% | 22% | 16% | 6% | 7% |
| polycaprolactone | 24% | 34% | 40% | 50% | 51% |
| PEG | — | 2% | 2% | 2% | 2% |
| Iron Oxide | — | 2% | 2% | 2% | — |
| Total | 100% | 100% | 100% | 100% | 100% |

TABLE 2

| | | BIOPIN-6 | BIOPIN-8 Composition | | |
|---|---|---|---|---|---|
| Composition | BIOPIN-6 | (with PEG) | B8-1 | B8-2 | B8-3 |
| naltrexone | 40% | 40% | 40% | 40% | 40% |
| poly(DL-lactide) | 36% | 35% | 40.6% | 46.4% | 52.2% |
| polycaprolactone | 24% | 23% | 17.4% | 11.6% | 5.8% |
| PEG | — | 2% | 2% | 2% | 2% |
| Total | 100% | — | 100% | 100% | 100% |

As shown in Tables 1 and 2, the BIOPIN formulation may include 2 wt. % of PEG to study the effect of the PEG ingredient on the drug release. Table 1 summarizes the composition of BIOPIN-6 and different BIOPIN-7 formulations. Table 2 summarizes the composition of BIOPIN-6 and different BIOPIN-8 formulations. Among different exemplary embodiments of the compositions, BIOPIN-6 and BIOPIN-8(2) may be preferred embodiments for the system of the present invention.

The unique implant composition has been optimized by using the polymers poly (LD-lactide) and polycaprolactone which are biodegradable. In addition, the implant composition includes the polymer PEG (numbered by the numeral 54 in FIGS. 1B and 3B) which is a plasticizer and anti-biofouling agent capable of reducing possible foreign absorption-interaction at the implant surface. In FIG. 3A, the blood plasma proteins 56 including immunoglobulin and complement proteins can interact with the implant surface 24, thus undermining the correct treatment protocol and possibly causing inflammation reaction of the patient to the foreign accumulations on the implant surface. Shown in FIG. 3B, when the implant composition includes PEG, this compound protects the implant surface 24 from interaction with blood clots, proteins, immunoglobulin, and complement proteins, and thus prevents possible foreign-body adsorption/interaction with the material of the implant 18.

The combination of polymers poly (LD-lactide) and polycaprolactone with naltrexone base anhydrous in predetermined weight percentages is not believed to have been formulated prior to the subject implant composition to provide the controlled dispersion of the medicinal composition based upon the ratio of the polymers poly (LD-lactide) to polycaprolactone dependent upon a selected treatment. Poly (LD-lactide) extends the dispersion time whereas Polycaprolactone shortens the dispersion time. The ratio of Poly (LD-lactide)/polycaprolactone provides for the controlled dispersion of the subject application system. Thus, for the purposes and objectives of the subject application, the ratio by weight percentage of the polymers poly (LD-Lactide) and polycaprolactone becomes a critical factor in controlling the medicinal composition release for a selected treatment protocol.

With use of the naltrexone, it has been found that for selected treatment protocols in combatting OUD, that the polymer poly (LD-lactide) in the weight range of 6% to 52.2% and the Polycaprolactone in the weight range of 5.8% to 51% of the entire poly (LD-lactide), polycaprolactone, and naltrexone composition provides for a highly controllable releasable composition for a selected protocol in combatting OUD. The combination of poly (LD-lactide)/polycaprolactone/naltrexone has been found to provide extremely high capabilities of controlling the dispersion of the medicine as opposed to the use of the medicine with only polymers poly (LD-Lactide) or polycaprolactone by themselves.

Clinical studies were conducted on the subject system 10 both in vivo experiments (animal-canine) and in vitro (dissolution). Due to optimized controllability of the medicinal agent release profile through formulation of the subject composition (both ingredients and their relative wt. % content) as well as due to the optimized process of manufacturing the solid highly homogeneous defect-free implant 18, the clinical studies confirmed successful treatment using the subject system 10. The fabrication process regime (process design space) has been optimized with regard to the temperature of the process and mixing time of the ingredients, as well as the injection time.

The present subcutaneous implantable medicinal dosage delivery implant system for the extended release of the medicinal agent is uniquely equipped for releasing of a medication over an extended period of time (for 12 month and over treatment duration, if needed) for the purpose of treating numerous medical conditions, where pharmacokinetics is controlled by varying the percentages of each of the various polymers, which is enhanced by embedding radiopaque localizer elements in the implant, here the implant contains an anti-fouling agent polyethylene glycol (PEG) to prevent any possible foreign-body absorption/interaction with the implant surface, and where the delivery of an increased serum level of naltrexone base anhydrous (NTX) is attained to mitigate effects of fentanyl consumed with heroin. The subject implant may be fabricated by a combination of hot melt extrusion and injection molding where the unique process design space (temperature regime, mixing time regime, and ejection time regime) is optimized to produce highly homogeneous and free of defects implants.

As shown in FIGS. 4 and 5A-5C, the present system is fabricated by a combination of processes of hot melt extrusion (HME) and injection molding using a custom-made mold. The subject process method is intended for obtaining at the final stage a highly homogeneous defect-free solid implant 18 having a unique product composition formulated for a highly controlled prolonged release profile, unique implant design. The subject manufacturing process has been optimized to provide a combination of the process temperature, mixing time, and injection time.

Figure 4:
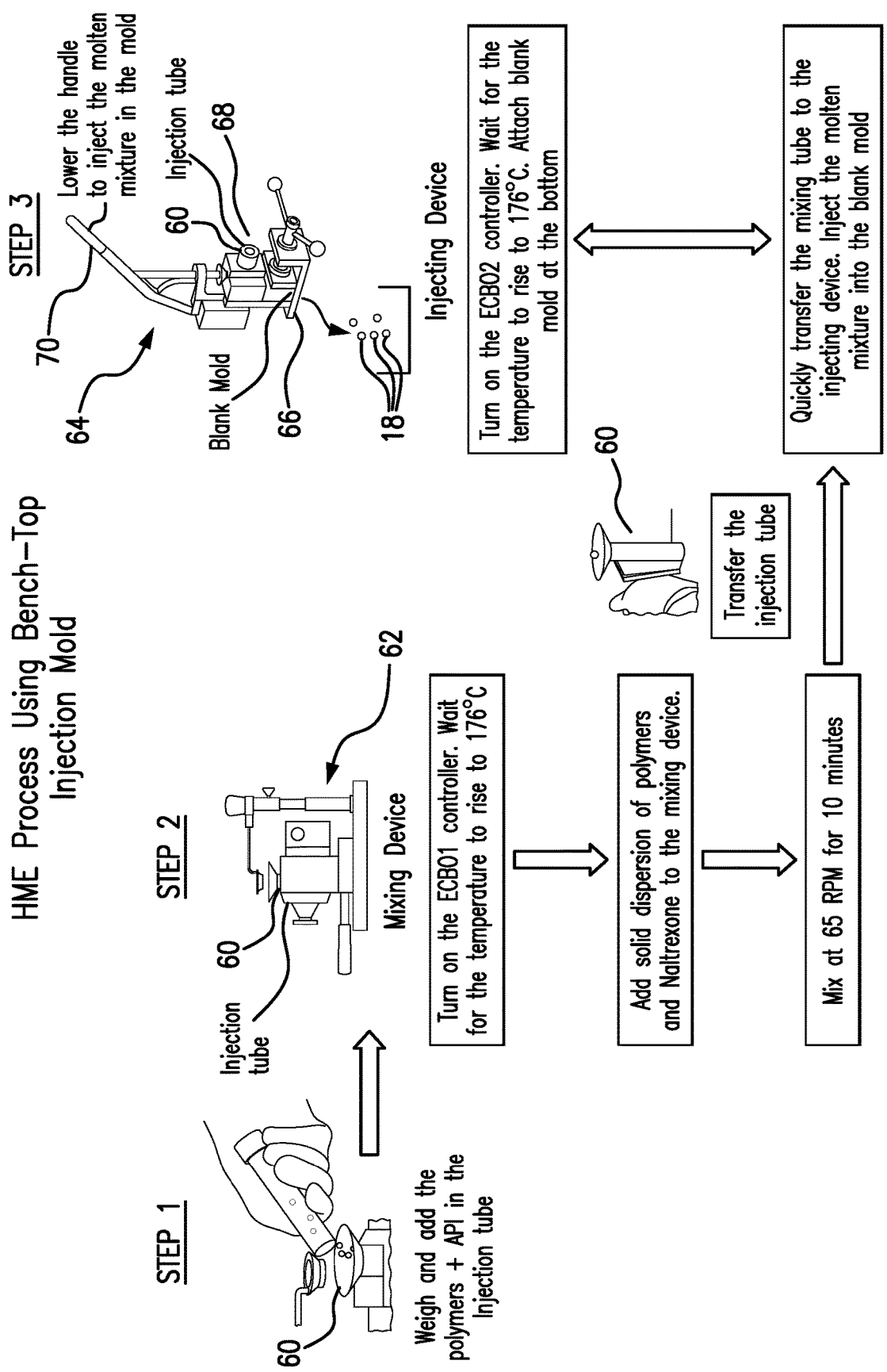
FIG. 4 is representative of the subject HME manufacturing process using bench-top injection mold.

Referring to FIG. 4, in one implementation, the present hot melt extrusion (HME) process uses bench-top injection mold. At Step 1, the ingredients (the medicinal agent, such as naltrexone base anhydrous, polymers poly (LD-lactide) compound, polycaprolactone compound, and PEG compound) are weighted and added in the injection tube 60. From Step 1, the procedure follows to Step 2 which uses a mixing device 62. Upon weighting and adding the polymers and the medicinal agent in the injection tube 60 in Step 1, in the subsequent Step 2, a controller in the mixing device 62 is turned on to establish the temperature of about 176° C., and the solid dispersion of polymers (polymers poly (LD-lactide), polycaprolactone, and PEG) and naltrexone in the injection tube is added in the mixing device 62. The solid dispersion is kept at 176° C. and mixed for about 10 minutes.

Subsequently, in Step 3, an injection device 64 is used. A blank mold is inserted in (or attached at) the blank mold portion 66 at the bottom of the injection device 64, and the injection tube 60 from the mixing device 62 is transferred to the injection device 64 and inserted in the injection tube section 68. The transfer of the mixture of the injection tube 60 to the injection device 64 is to be performed as quickly as possible in order to keep the temperature of the mixture in the injection tube 60 at the predetermined level of 176° C., which corresponds to the temperature of the injection device 64.

In order to inject the molten mixture from the injection tube 60 into the blank mold at the section 66, the handle 70 is lowered in the injecting device 64 and the molten mixture from the injection tube 60 is injected into the blank mold at the blank mold section 66 where it is formed into the resulting implant 18, and subsequently is output when cooled.

Figure 5A:
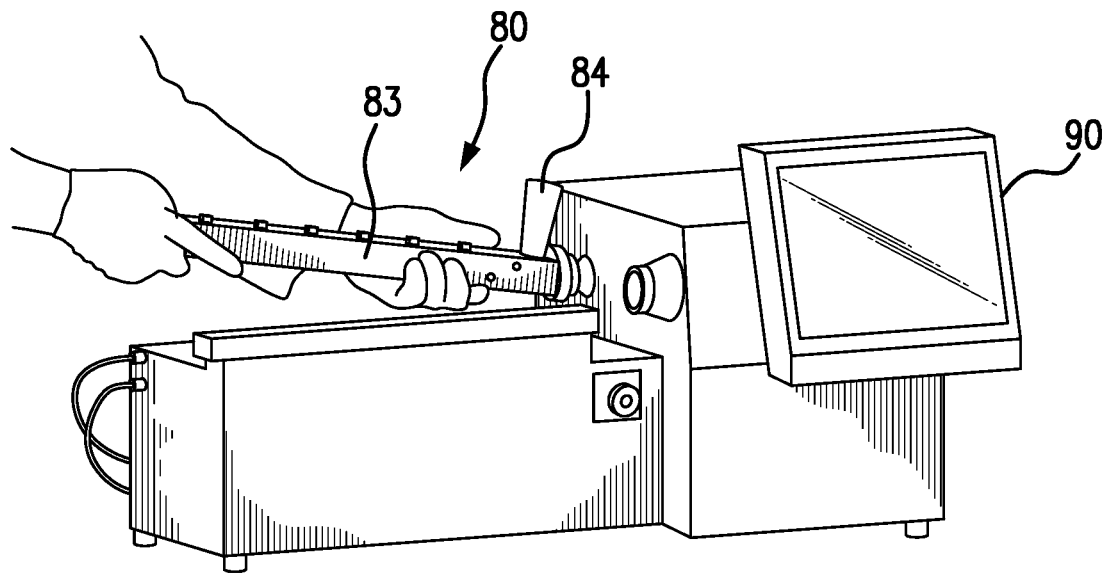
FIGS. 5A-5C are representative of the alternative HME process using Thermo Fisher equipment trains, with FIG. 5A showing the removal and/or replacing of the barrel of the twin screw extruder, FIG. 5B detailing the subject process equipment, and FIG. 5C detailing the twin screw extruder design used in the subject process.
Figure 5B:
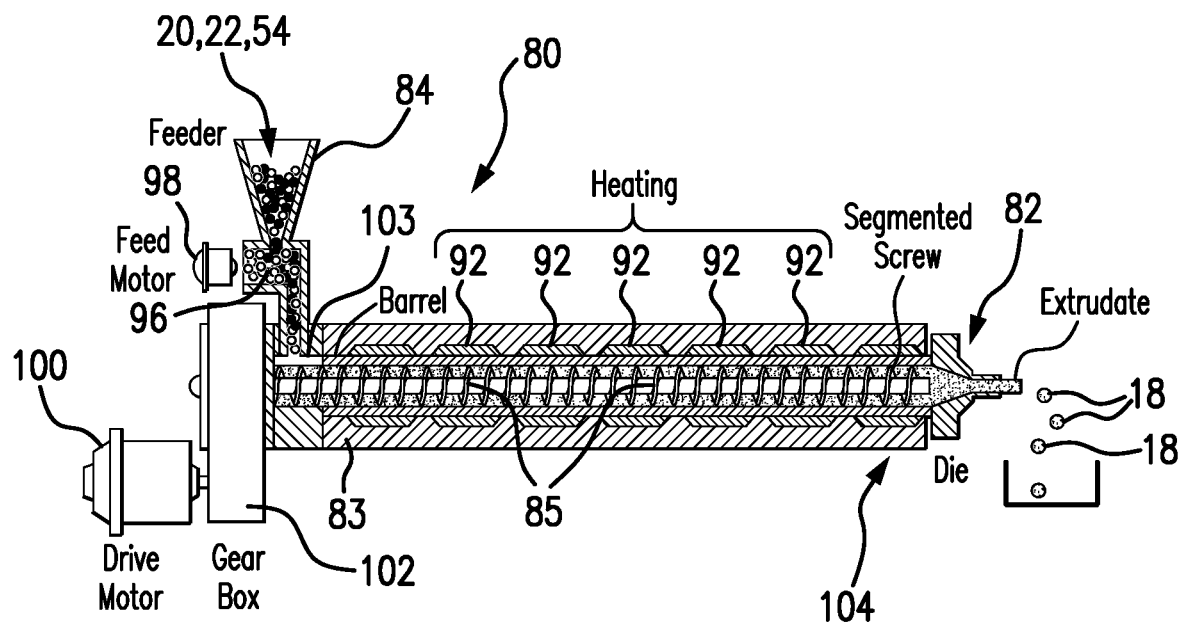
Figure 5C:
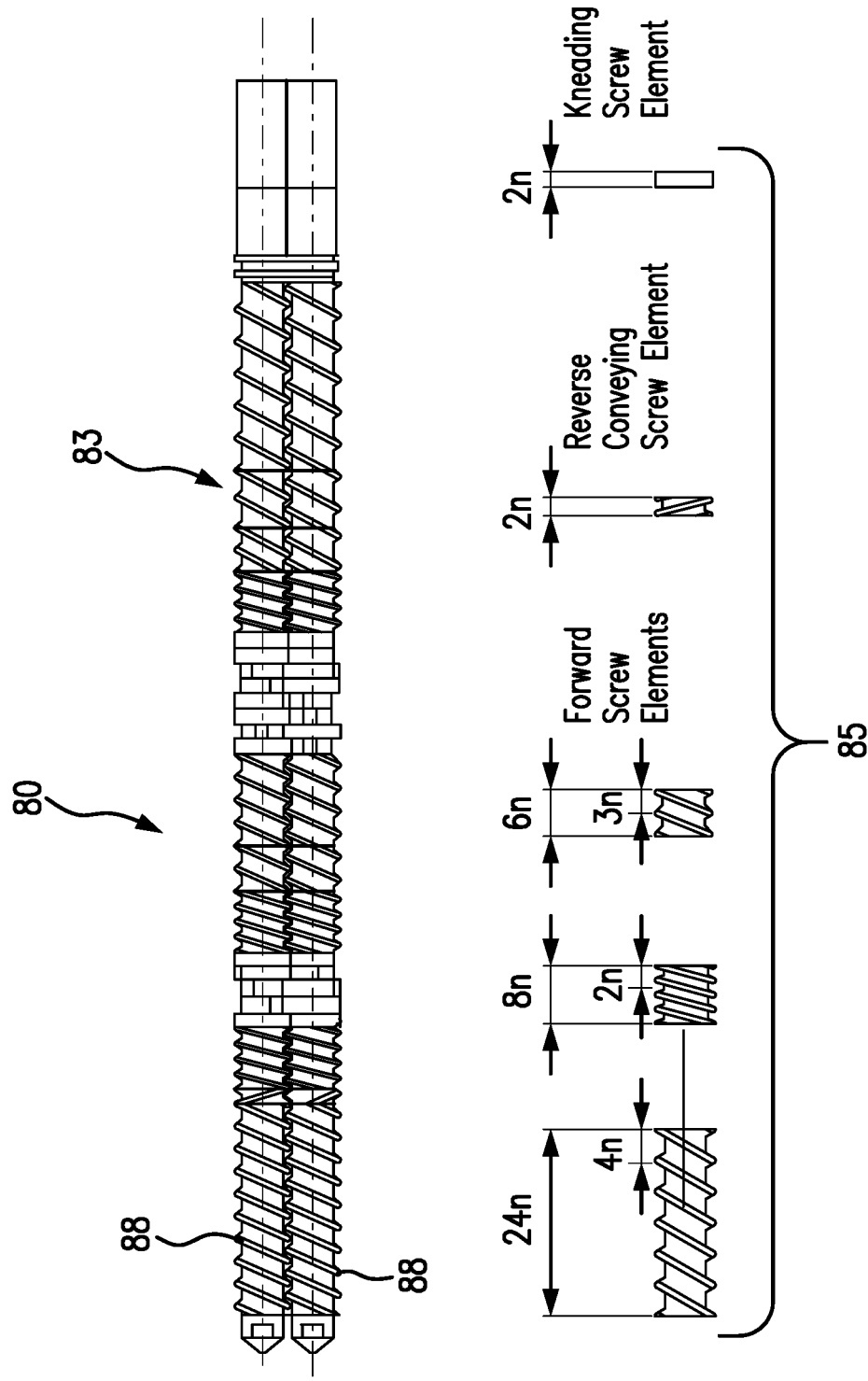

Alternatively, the HME process may use Thermo Fisher equipment shown in FIGS. 5A-5C accompanied by a mini-jet implant formatting unit. This equipment provides the hot melt extrusion processing of polymeric materials above their glass transition temperature in order to affect a molecular level mixing of thermoplastic polymers and the medicinal agent. The HME in this process is a combination of the melting and the mechanical energy to improve continuous processing for a reproducible analysis of materials and on-line monitoring.

The HME process is used to disperse API (medicinal agents) in a matrix at the molecular level thus forming a solid solution. As shown in FIGS. 5A-5C, the process uses an extruder 80 and the die in the configuration of a mini-jet implant formation unit 82. In the subject HME process shown in FIGS. 5A-5C, the medicinal agent 20 and the polymers 22, 54 are weighted and supplied to a feeder 84. All components 20, 22, 54 are sheared, heated, mixed, and dispersed, and finally shaped by pressing them through the die opening (mini jet) 82 to form implants 18.

Developing the HME manufacturing process requires control of numerous process parameters that affect the resulting implant. A computer system 90 controls and monitors the process parameters, which may be input in the computer system by an operator. Among the most important parameters which influence the quality of the resulting product, i.e., the implant 18, are mechanical energy consumption parameters, such as the temperature of the melt at the extruder die, pressure at the die, the torque in the extruder. The injection time at the die and mixing time are also among the process parameters which are critical for the quality of the resulting implant.

As shown in FIGS. 5A-5C, the system underlying the subject HME process uses a twin-screw extruder 80 encased in a barrel 83 which can be easily inserted in and removed from the equipment as presented in FIG. 5A. As depicted in FIG. 5C, the twin screw extruder 80 is designed with various screw elements 88 of different predetermined dimensions connected into a sequence train which provides mixing elements with configurable shear rates along the barrel's length. The screw elements 88 constitute a plurality of mixing/shearing zones 85 having different dimensions for mixing/shearing the mixture received from the feeder 84 with controllable shear rates which provide an optimal mixing of the mixture of the API 20, the medicine release controlling polymers 22 and PEG 54 of the subject formulation composition at the molecular level.

In addition to the number of the mixing/shearing zones 85, the HME process equipment may have a number, for example, six, heating zones 92 of different temperature configurations provided along the twin screw extruder 80. The computer control block 90 interfaces with a user who establishes regimes for various heating zones 92 while the composition passes these zones.

The feeder 84 is disposed at the beginning of the HME process s for forming the initial mixture of the medicinal agent (API) 20, polymer compounds 22 and PEG 54. Preferably, the feeder 84 is a dual feeder with separate inlet and temperature control for the medicinal agent and polymers, respectively. In the chamber 96 of the feeder 84, the initial mixture is exposed to the mixing action by the feed motor 98. From the chamber 96, the mixture of the medicinal agent 20 and the polymers 22, 54 passes to the entrance of the barrel 83 with the twin screw extruding structure 80 detailed in FIG. 5B-5C.

The twin-screw extruder 80 is actuated into the rotational motion of the screws 88 through the action of the drive motor 100 connected to the gear box 102. The mixture of the API (naltrexone) and the polymers (poly (LD-lactide), polycaprolactone, and PEG) passes from the chamber 96 into the twin-screw extruder 80 and, by the rotational motion of the screws 88, advances from the entrance of the extruder 80 to its exit 104. The mini jet 82 is positioned at the end 104 of the extruder 80. The mini jet 82 serves as a die (mold) for forming the implants 18 in the preferred shape (as shown in FIGS. 2A-2D), which are output from the die 82.

Figure 6:
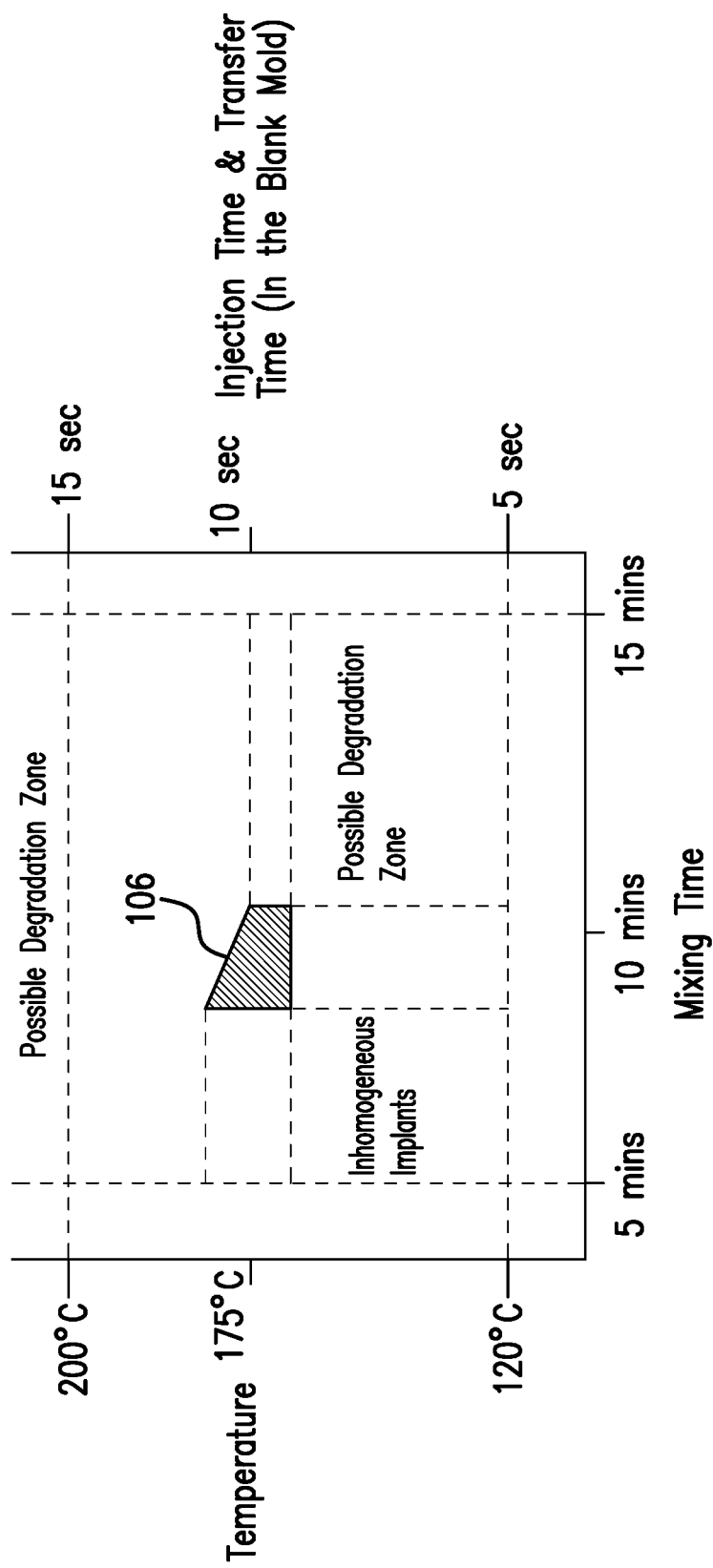
FIG. 6 is a diagram representative of the optimized manufacturing process technological parameters.

The process presented in previous paragraphs has been optimized with the unique process design space shown in FIG. 6. The HME process boundary for the optimal process producing the defect-free highly homogeneous product (implant) 18, depends on numerous parameters of the process, including the speed of the screws 88, mixing time in the extruder 80, injection time at the die 82, as well as the temperature at the heating zones 92, etc. The current manufacturing process has been analyzed and studied and optimized with a unique process design where the temperature in the extruder 80 changes between 170° C. and 180° C., with the mixing time in the extruder 80 ranging between 8 minutes and 12 minutes, and the injection time (in the die 82) ranging between 8 seconds and 12 seconds. Manufacturing in conditions outside the zone 106 shown in FIG. 6 may either result in the defective or inhomogeneous implants.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. A method of fabrication of an extended-release subcutaneous medicinal dosage delivery implant system, comprising:
   (a) mixing at least one medicinal agent and release controlling polymeric compounds in a feeder to form an injection mixture,
   (b) injecting said injection mixture into a segmented screw extruder having a first plurality of heating zones and a second plurality of mixing/shearing zones, each mixing/shearing zone creating a specific predetermined shear rate,
   (c) actuating said segmented screw extruder,
   (d) advancing said injection mixture along said actuated segmented screw extruder from an input to an output thereof during a mixing time ranging from 8 min to 12 min,
   (e) exposing said injection mixture to a temperature regime ranging from 170° C. to 180° C. while passing through said plurality of heating zones, thus forming a melted homogenous injection mixture,
   (f) installing a mini-jet implant formation unit at said output of said segmented screw extruder, and
   (g) forming a highly homogeneous solid implant in said mini-jet implant formation unit by passing said melted homogeneous injection mixture therethrough during an injection time ranging between 8 sec and 12 sec.

2. The method of claim 1, further comprising:
   in said step (a), heating said at least one medicinal agent to a first temperature of 176° C.±5° C. and heating said release controlling polymeric compounds to a second temperature of 176° C.±5° C.

3. The method of claim 1, further comprising in said step (g), forming said solid implant having a smooth surface devoid of sharp areas.

4. The method of claim 1, further comprising:
   in said step (a), adding an anti-fouling agent containing polyethylene glycol (PEG) in said injection mixture.

5. The method of claim 1, wherein said medicinal agent includes naltrexone base anhydrous.

6. The method of claim 1, wherein said release controlling polymeric compounds include at least poly (DL-lactide) in a weight % ranging from 6% to 52.2%, and polycaprolactone in a weight % ranging from 5.8% to 51%.

7. The method of claim 6, wherein in said step (a), said injection mixture is formed by mixing 40 weight % of naltrexone, 36 weight % of poly (DL-lactide), and 24 weight % of polycaprolactone.

8. The method of claim 6, wherein said injection mixture is formed by mixing approximately 40 weight % of Naltrexone, approximately 46.4 weight % of Poly (LD-Lactide), approximately 11.6 weight % of Polycaprolactone, and approximately 2 weight % of Polyethylene Glycol (PEG).

* * * * *